United States Patent [19]
Yonekawa et al.

[11] Patent Number: 5,388,164
[45] Date of Patent: Feb. 7, 1995

[54] METHOD FOR JUDGING PARTICLE AGGLUTINATION PATTERNS USING NEURAL NETWORKS

[75] Inventors: Hiroyuki Yonekawa, St. James; Christopher M. Skoldberg, Hauppage, both of N.Y.

[73] Assignee: Olympus Optical Co., Ltd., Tokyo, Japan

[21] Appl. No.: 932,414

[22] Filed: Aug. 19, 1992

[51] Int. Cl.$^6$ .......................................... G01N 33/80
[52] U.S. Cl. .......................................... 382/6; 382/14
[58] Field of Search .................. 382/6, 14, 15; 356/39

[56] References Cited

U.S. PATENT DOCUMENTS

| | | | |
|---|---|---|---|
| 4,466,740 | 8/1984 | Kano et al. | 356/39 |
| 4,965,725 | 10/1990 | Rutenberg | 382/36 |
| 5,096,835 | 3/1992 | Yokonori et al. | 356/39 |

*Primary Examiner*—David K. Moore
*Attorney, Agent, or Firm*—Kenyon & Kenyon

[57] ABSTRACT

Particle patterns formed on an inclined bottom surface of a reaction vessel are photoelectrically detected to produce a two-dimensional image signal. The signal is processed to judge or classify the particle patterns into an agglutinated pattern, a non-agglutinated pattern or an uncertain pattern with the aid of a neural network. An image signal representing a particle pattern is first extracted, then the image signal is decomposed into a series of light intensity areas due to different contours of the inclined bottom surface. The integrated light intensities of each area are presented to a neural network. The neural network operates in a training mode and a classification mode. In the training mode the neural network is presented with numerous samples of decomposed images as well as their respective classification. In the classification mode the neural network will judge a decomposed image based on a generalization made during the training mode.

4 Claims, 5 Drawing Sheets

0.05 mm 4.5 mm

Sample 1
Non-Agglutinated

Sample Image

Sample 2
Agglutinated

Feature Vector Histogram
(normalized to unity)

Sample 3
Uncertain

Sample Image

Sample 4
Uncertain

Feature Vector Histogram
(normalized to unity)

FIG. 6
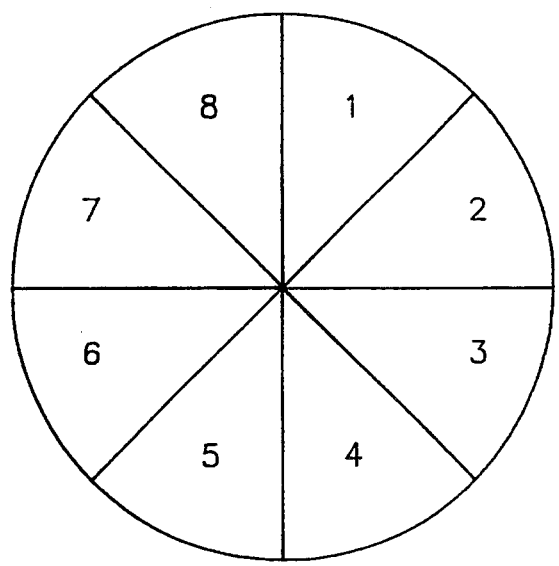
FIG. 7
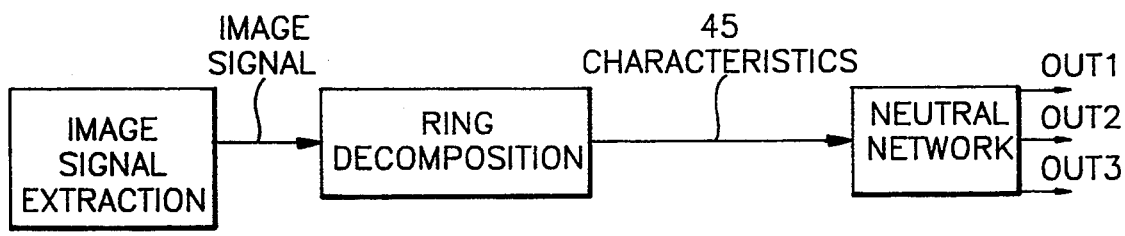
FIG. 8

METHOD FOR JUDGING PARTICLE AGGLUTINATION PATTERNS USING NEURAL NETWORKS

BACKGROUND OF THE INVENTION

1. Field of the Invention

The present invention relates to a method of detecting and judging a particle agglutination pattern for use in diagnosis.

2. Description of Related Art

An apparatus has been developed for analyzing a blood sample by detecting a particle agglutination pattern formed on a reaction vessel having an inclined bottom surface. Such an apparatus is described in, for instance, U.S. Pat. No. 4,727,033 issued to K. Hijikata et al. on Feb. 23, 1988. In this apparatus, a test liquid is formed in a conical reaction vessel by supplying a blood sample (i.e., a blood cell sample or serum sample) and a reagent (i.e., a serum reagent or sensitized particle reagent) into the reaction vessel, and maintaining the reaction vessel containing the test liquid stationary for a predetermined reaction time such as thirty minutes. During the reaction time, particles in the test liquid descend onto the inclined bottom surface. When the particles agglutinate, they form a uniformly agglutinated layer on the bottom surface, but when the particles are not agglutinated with each other they roll down along the inclined bottom surface and are collected at the lowest bottom center to form a center dot. Next, the particle pattern formed on the bottom surface of the reaction vessel is photoelectrically detected by projecting light from one side of the reaction vessel and light transmitted through the reaction vessel is received by a photodetector.

For this purpose, U.S. Pat. No. 4,727,033 discloses a photodetector having two concentrical light receiving regions, one for receiving light passing through a central portion of the reaction vessel and the other for receiving light transmitted through a peripheral portion of the reaction vessel. By processing output signals supplied from these light receiving regions, it is possible to determine whether the particle pattern is agglutinated or non-agglutinated. When the particles are agglutinated, there is no significant difference between the output signals from the two light receiving regions. On the other hand, when a non-agglutinated particle pattern is formed, the light passing through the central portion of the reaction vessel will be attenuated to become weaker than the light transmitted through the peripheral portion, thereby resulting in a large difference between the output signals supplied from the two light receiving regions.

Therefore, by obtaining a ratio of the output signal from the central light receiving region to the output signal from the peripheral light receiving region and comparing the ratio with predetermined upper and lower thresholds, the particle pattern formed on the inclined bottom surface can be determined and the blood sample can be analyzed. When the ratio is greater than the upper threshold value, this is indicative that agglutination occurs, and when the ratio is smaller than the lower threshold value, this is indicative that agglutination does not occur. When the measured ratio is within the upper and lower threshold values, it is indicative that the particle pattern could not be determined with certainty.

An improved method of judging particle patterns can be found in Japanese laid-open Patent Tokkai-hei 03-056843 which corresponds to U.S. patent application Ser. No. 384,497 filed on Jul. 25, 1989. This method consists of photoelectrically scanning the particle pattern to derive an image signal representing a two-dimensional image including the whole particle pattern. The image signal is then processed to derive at least two characteristics of the particle pattern, and then the particle pattern is judged on the basis of these characteristics.

One of the characteristics is the ratio of the average output signal from the center of the image signal to the average output signal from the periphery of the image signal. This is similar to the ratio used in accordance with U.S. Pat. No. 4,727,033 described above, with the same threshold judgement techniques. The two dimensional image signal allows for more of the particle pattern to be used in the ratio calculation, thereby improving the judgement accuracy. The second characteristic is the measurement of the sharpness of the center dot. If the sharpness of center dot from a particle pattern is above a predetermined threshold, it is indicative that agglutination did not occur. If the sharpness of center dot from a particle pattern is below a predetermined threshold, it is indicative that agglutination did occur. If the two characteristics, namely the ratio and the sharpness, are in contradiction, it is indicative that the particle pattern cannot be certainly determined.

It has been experimentally confirmed that the two known methods, described above, of judging particle patterns are suitable for judging true or typical particle patterns. However, in the actual analysis, sometimes particle patterns are produced which cannot be definitively judged by either of the two known methods. In such a case, an automatic analysis result is generated indicating that the relevant sample could not be determined with certainty, so that the sample has to be analyzed visually with the naked eye or has to be retested. In order to increase the efficiency of the analysis, it would be desirable to reduce the number of samples which need to be analyzed again. In the two known methods, this may be effected by changing the threshold values for use in the comparison, however, the accuracy of the analysis would then be compromised by erroneous determinations.

SUMMARY OF THE INVENTION

The primary object of the present invention is to provide a novel and useful method of detecting and judging a particle pattern formed on an inclined bottom surface of a reaction vessel in a reliable and economical manner, which reduces the number of samples which would otherwise need to be retested or analyzed by the naked eye so as to maximize the accuracy of the analysis.

The present invention achieves this objective by adopting a neural network into a judging method of a particle pattern. The invention provides a method of determining a particle pattern formed on an inclined bottom surface of a reaction vessel, which comprises the steps of:

photoelectrically scanning the inclined bottom surface to derive an image signal which represents a two-dimensional image of the particle pattern;

processing the image signal into area light intensities by separating the inclined bottom surface into a plurality of areas due to different contours of the inclined bottom surface and integrating light intensities in each area to derive the area light intensities;

inputting the area light intensities into a neural network to produce output signals; and determining an agglutination reaction based on the output signals.

In the method according to the invention, wherein said neural network had been trained such that area light intensities of a given number of particle patterns and corresponding true judgment of the given number of particle patterns were inputted into said neural network for training. In this way, as the given number of particle patterns that are inputted into said neural network for training is increased, the number of samples which ordinarily have to be reanalyzed by the naked eye decreases and the accuracy of the analysis increases.

BRIEF DESCRIPTION OF THE DRAWINGS

FIG. 6 is a plan view showing another embodiment of the invention in the form of square light intensity areas.

FIG. 7 is a plan view showing a variation in the form of pie wedge light intensity areas for comparison with the invention.

FIG. 8 is a block diagram showing another embodiment of the judging operation of the invention.

DETAILED DESCRIPTION OF THE PREFERRED EMBODIMENTS

Figure 1:
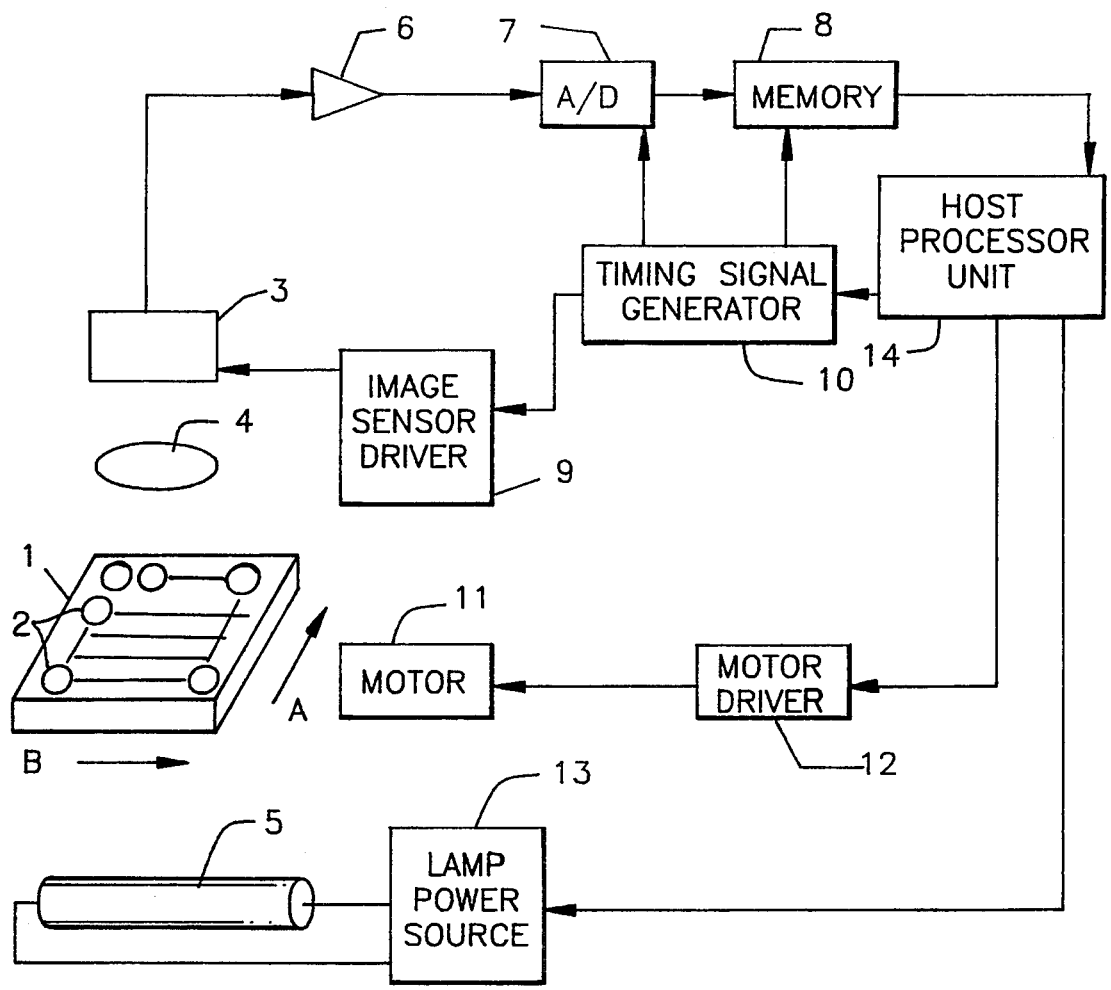
FIG. 1 is a block diagram showing an apparatus for carrying out the method according to the invention.

FIG. 1 is a block diagram showing the construction of an embodiment of the apparatus for carrying out the method according to the invention. In this embodiment, use is made of a microplate 1 in which a number of wells 2 serving as reaction vessels are formed in a matrix. It should be noted that the method according to the invention can also be carried out with various kinds of reaction vessels other than the microplate.

Figure 2:
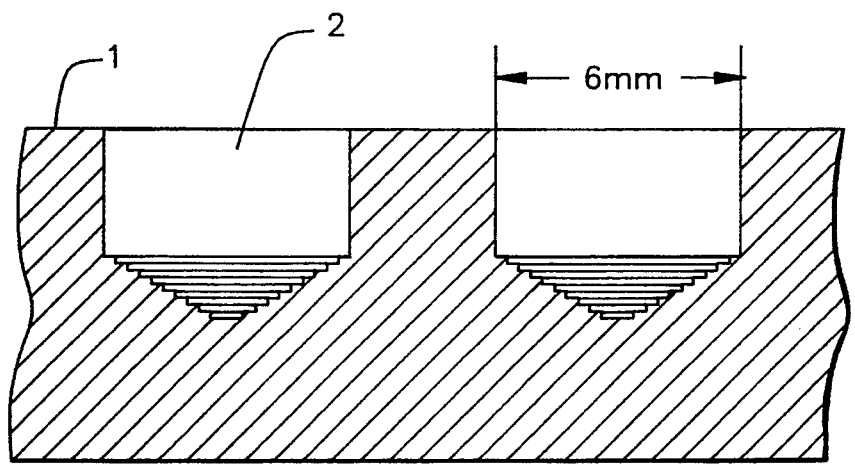
FIG. 2 is a cross-sectional view illustrating wells formed in the microplate for use in the apparatus shown in FIG. 1.

Referring to FIG. 2, a cross-sectional view of the well 2 formed in the top surface of the microplate 1 is illustrated. The well 2 has a conical bottom surface in which a number of fine steps are uniformly formed in order to form a basic layer of particles, the basic layer being particularly suitable for forming a stable agglutinated particle pattern. In the present embodiment, the diameter of the well 2 is 6 mm, and the microplate 1 is made of transparent material like clear acrylic resin or glass.

In the present embodiment, the image of the microplate 1 is picked up by a photoelectric image detecting device, including a solid state image sensor 3, a lens 4 placed in front of the image sensor and an illumination lamp 5 arranged underneath the microplate 1. The microplate is moved in directions A and B to provide the capability to capture an image of each and every reaction vessel. A conventional mechanism 11, 12 for driving the microplate 1 is provided. In addition, various kinds of devices for supplying the microplate 1 onto a reaction line (not illustrated), for delivering sample liquid and reagent liquids into the wells 2 (not illustrated) and for transporting the microplate along the reaction line (not illustrated), all of which are well known in the art, may be provided. For example, these devices may be those illustrated in the above mentioned U.S. Pat. No. 4,727,033 discussed above.

The apparatus further comprises an amplifier 6 which supplies an image signal to an analog-digital converter 7 and a converted digital image signal is stored in an image memory 8. The solid state image sensor 3 is driven by a driver circuit 9 which is controlled by a timing signal generator 10. The analog-digital converter 7 and memory 8 are also controlled by the timing signal generator 10. The microplate 1 is driven in directions A and B by a motor 11 which is energized by a motor driver 12. An illumination lamp 5 comprising a fluorescent lamp is energized by a lamp power source 13.

In order to operate the above mentioned circuit elements in conjunction with each other, there is provided a host processor unit 14. The image signal stored in image memory 8 is digitally processed by the host processor unit 14 in order to judge the particle pattern formed at the bottom of the reaction vessel 2. The operation of the host processor unit 14 will be explained in detail.

Figure 3:
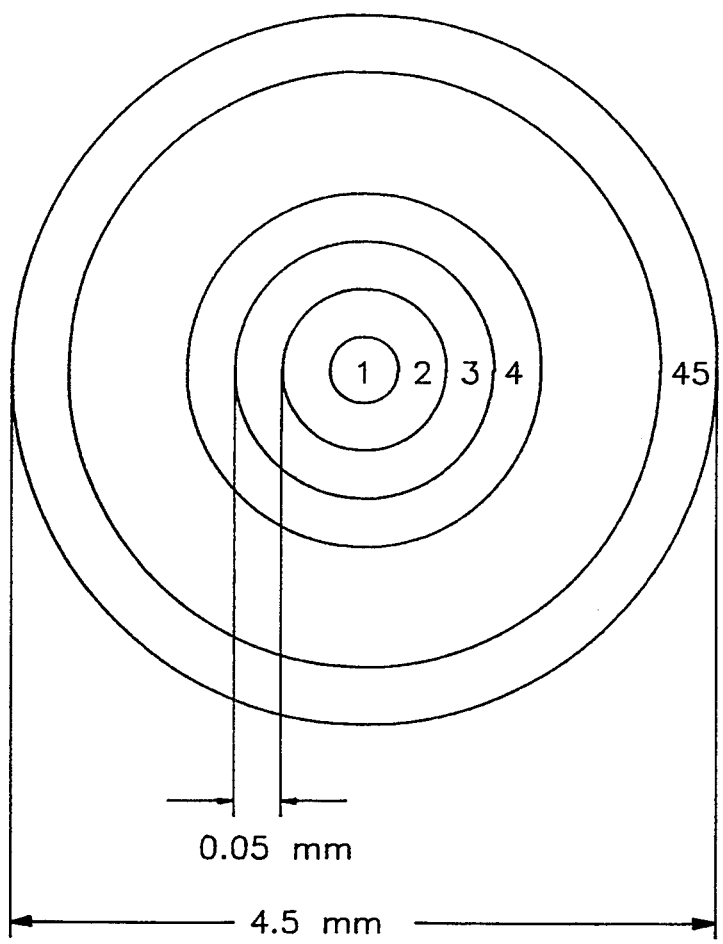
FIG. 3 is a plan view showing the series of rings used to decompose the image signal of the particle pattern from the well shown in FIG. 2 into 45 light intensity areas representing different contours of the conically inclined reaction vessel.

In order to determine the particle pattern by means of a neural network, it is advantageous to decompose the two-dimensional image of the particle pattern into a series of concentric rings. In the present embodiment, 45 rings were experimentally determined to produce desirable results. Other numbers of rings may be applicable. The photoelectric device is centered above the conically inclined bottom surface of the reaction vessel such that the inner most ring of the decomposed two-dimensional image will represent the center of the reaction vessel. FIG. 3 is a plan view showing the series of concentric rings. FIG. 2 is a plan view showing the cross section of the reaction vessel. In the present embodiment, each ring has a width of 0.05 mm and the total width of all rings is 4.5 mm. Calculating the average intensity of each ring will form 45 characteristics of the particle pattern representing the distribution of particles from the center of the conically inclined bottom surface. These 45 characteristics of the particle pattern become the inputs to the neural network.

The neural network used in the invention is a standard back-propagation network. A back-propagation neural network is organized for pattern classification. In this embodiment, the neural network is constructed in a host processing unit 14, which consists of hardware (model name 486/33, available from GATEWAY 2000) and a neural network software package (Neural Works, available from Neural Ware Inc.). It may be trained with analyzed results as standard or control data. It is available to train the neural network by an external teacher in the form of a human operator or the naked eye with one's judgment. General neural networks may be used in this inventions. Other commercially available neural network software packages include ANSim (available from Science Applications International Corporation) and MacBrain (available from Neurix).

Figure 4:
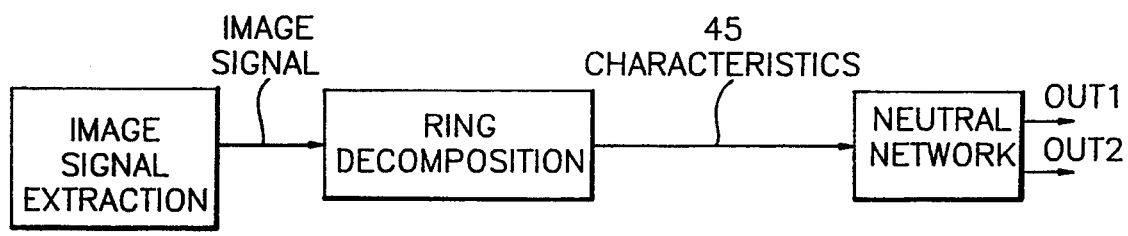
FIG. 4 is a block diagram showing the judging operation.

The neural network has been configured such that the inputs must be between 0 and 1. Therefore, the 45 characteristics must first be normalized between 0 and 1, with the largest characteristic taking on the value of 1 and the other characteristics maintaining the same proportion to the largest characteristic. The neural network was designed to include 45 inputs and 2 outputs. The outputs are also limited to values between 0 and 1. FIG. 4 is a block diagram representing the determination of the particle pattern by extracting the 45 characteristics of the image of the particle pattern and then using a trained neural network to produce 2 output signals which are used to judge an agglutination reaction.

Figure 5A:
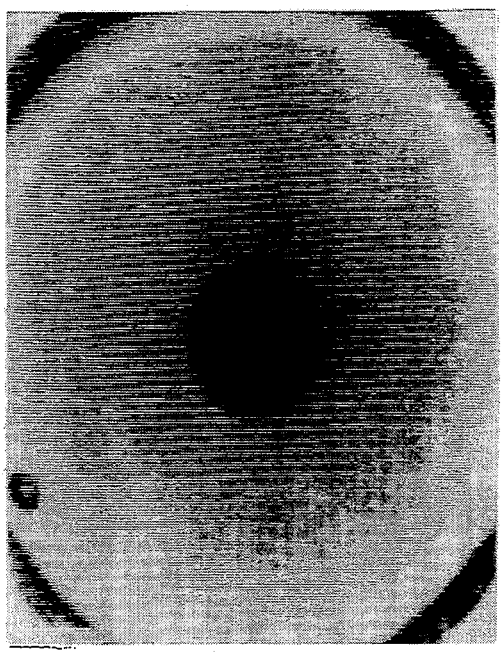
FIGS. 5A–5H are photographs representing various particle patterns and their respective area light intensity values.
Figure 5B:
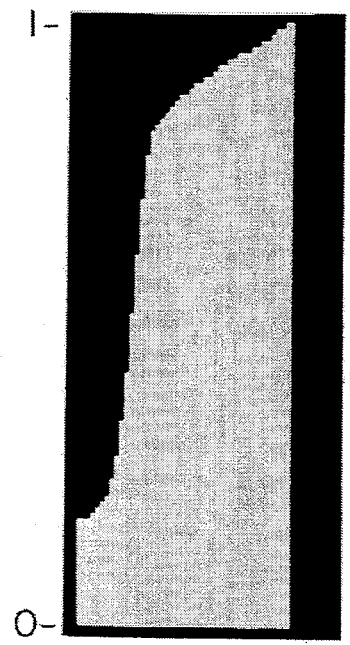

FIGS. 5A–H are photographs of sample particle patterns with their respective 45 characteristics shown as a histogram with values between 0 and 1. The left most characteristic represents the first and inner most ring and the right most characteristic represents the last and outer most ring. In particular, FIG. 5A is a photograph of a typical non-agglutinated particle pattern in which the particles have migrated to the center or the bottom of the reaction vessel. FIG. 5B shows the resultant 45 characteristics in which the left most values are closer to 0, in sharp contrast to the right most values which are closer to 1. This is representative of the darkness in the middle of the particle pattern due to the clustering of the particles to the center of the reaction vessel.

Figure 5C:
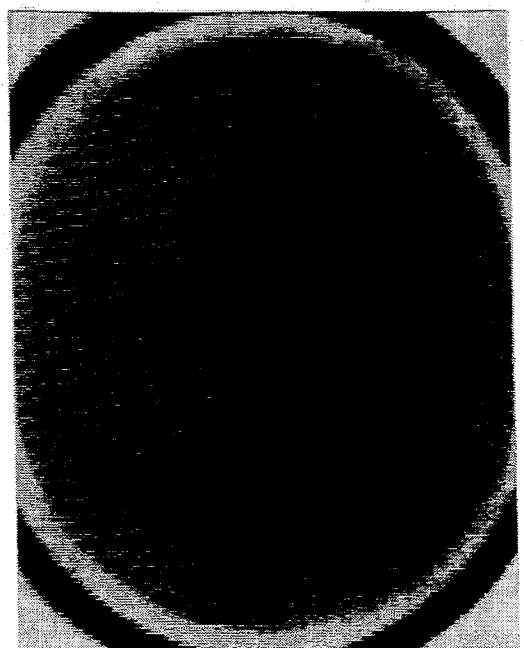
Figure 5D:
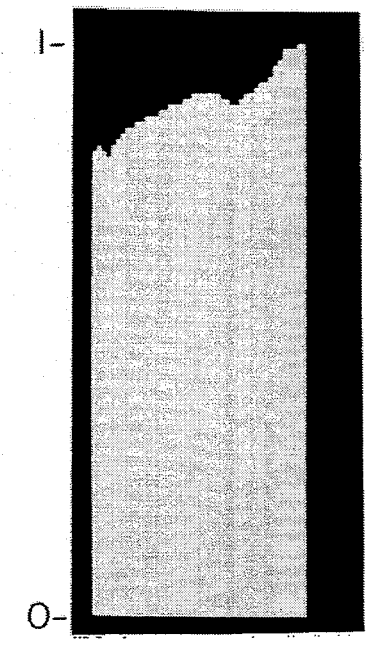

FIG. 5C is a photograph of a typical agglutinated particle pattern in which the particles are uniformly distributed on the bottom surface of the reaction vessel. The resultant 45 characteristics shown in FIG. 5D show a corresponding even distribution.

Figure 5E:
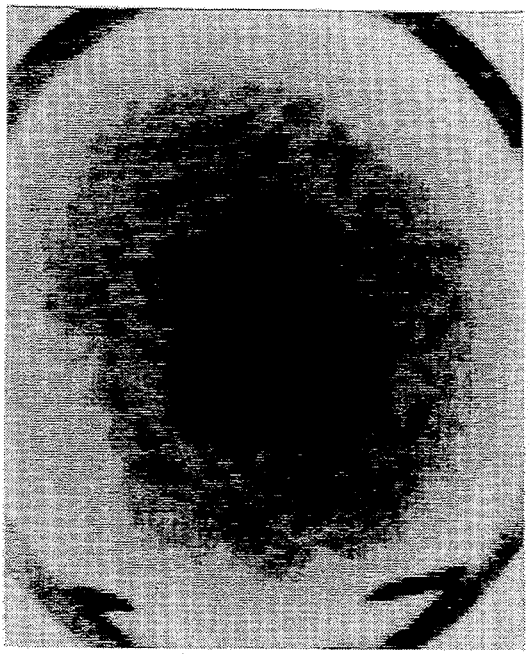
Figure 5F:
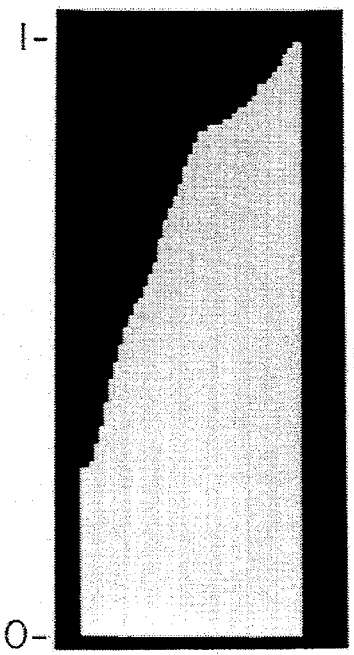
Figure 5G:
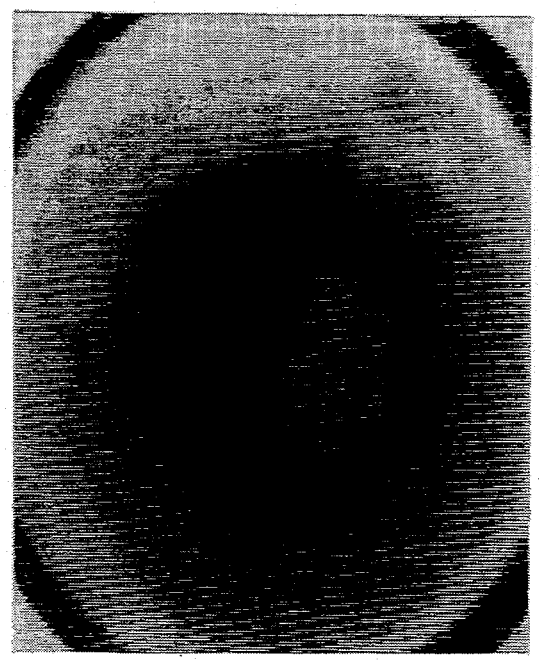
Figure 5H:
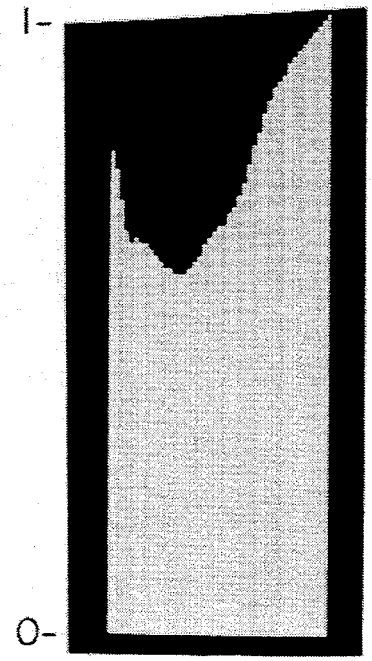

FIGS. 5E and 5G are photographs of typical uncertain particle patterns with their corresponding 45 characteristics shown in FIGS. 5F and 5H respectfully. An uncertain particle pattern is generally any pattern that is not judged to be either agglutinated or non-agglutinated.

In order for the neural network to determine the particle patterns in the above-described manner using the said 45 inputs and 2 outputs, it must first be trained with standard samples or with plural samples by the aid of a human operator's judgment. The neural network is trained by presenting to it numerous standard samples of agglutinated, non-agglutinated and uncertain samples or non-standard plural samples. Each sample presented to the neural network is in the form of its said 45 characteristics and 2 outputs, Out1 and Out2. If the agglutinated standard sample is used or if the human judgment of a sample is agglutinated, then the two desired outputs are Out1=1 and Out2=0. If the non-agglutinated standard sample is used or if the human judgment of a sample is non-agglutinated, then the two desired outputs are Out1=0 and Out2=1. If the uncertain standard sample is used or if human judgment of a sample is uncertain, then the two desired outputs are Out1=0 and Out2=0.

Once the neural network has been trained, it can be presented with new samples and will make a determination of the pattern of those samples based on a generalization made during its training. When the neural network is called upon to make a judgment, it is presented with the 45 characteristics of a sample and a judgment can be determined from the values of its two outputs in accordance with Table 1.

TABLE 1

| OUT1 | OUT2 | JUDGMENT |
| --- | --- | --- |
| 1 | 0 | + (positive) |
| 0 | 1 | − (negative) |

TABLE 1-continued

| OUT1 | OUT2 | JUDGMENT |
| --- | --- | --- |
| 0 | 0 | ? |

Note:
+ means agglutination.
− means non-agglutination.
? means uncertain.

There is another way to decide the particle pattern using a certain threshold value. It is effective in the case in which OUT1 and OUT2 takes intermediate values between 0 and 1 even if after the training. For example, if the first output is above a predetermined threshold, then the particle pattern is judged to be agglutinated. If the second output is above the threshold, then the particle pattern is determined to be non-agglutinated. If both outputs are below the threshold, then the particle pattern is judged to be uncertain. Both outputs are never simultaneously above the threshold. In this embodiment, the value of the predetermined threshold is 0.98 and has been experimentally determined to give the best results.

EXAMPLE

An experiment was performed to determine the accuracy of the invention in comparison to the techniques described in Japanese laid-open Patent Tokkai-hei 03-056843, which shall be referred to herein as the Ratio Technique, and in comparison to variations of the invention. FIG. 6 is a plan view of a different embodiment of the invention which depicts a decomposition of the two-dimensional image of the particle pattern into a matrix of 49 squares, for comparison with the invention. The average intensity of each square makes up 49 characteristics of the particle pattern and can be used in conjunction with a neural network in a method similar to the described invention. FIG. 7 is a plan view of a variation of the manner of division which is for comparison with the invention. It depicts a decomposition of the two-dimensional image of the particle pattern into a pie of 8 equal wedges. The average intensity of each wedge makes up 8 characteristics of the particle pattern which are added to the 45 characteristics of the invention to form 53 characteristics and can be used in conjunction with a neural network in a method similar to the described invention. The 8 pie wedges in and of themselves are not capable of being trained for classification.

The neural networks of a series of rings, a matrix of squares, a series of rings+pie wedges, and a prior art ratio technique were each trained with 67 sample particle patterns with an approximate distribution of an equal amount of agglutinated, non-agglutinated and uncertain judgments. Then each neural network and the Ratio Technique was tested in the judgment of 165 different samples of which 79 were uncertain judgments. The results are shown in the following Table 2.

TABLE 2

| Method | Judgment Accuracy |
| --- | --- |
| Series of Rings | 96% |
| Ratio Technique | 89% |
| Matrix of Squares | 83% |
| Series of Rings + Pie Wedges | 96% |

The table shows that the series of rings exhibits the highest accuracy of all the techniques. The variation using the pie wedges gives the same degree of accuracy but with the disadvantage of requiring more calculations than the method of the invention. The invention also has an advantage over the Ratio Technique in that its accuracy may be further improved. If one takes the samples that were incorrectly judged by the invention, add them to the training set and retrain the neural network, the invention's accuracy may be further improved. The advantage is attributable to the division of the inclined bottom surface such that the image signals are processed into area light intensities by separating the inclined bottom surface into a number of areas which represent different contours of the inclined bottom surface.

With regard to the matrix of squares embodiment of the invention, it should be appreciated that although the judgment accuracy reported in Table 2 was only 83%, this result can be improved significantly if additional training for the neural network is conducted. In this regard, it can be seen that in this Example only 67 particle pattern samples were used in the training.

The invention was also compared to the other techniques in terms of computational efficiency. The determination of a sample can be achieved 10 times faster using the invention as compared to the Ratio Technique. This is an advantage that can increase the throughput of a device for analyzing multiple samples or that would allow for a more economical device at the same throughput. Notwithstanding the 83% accuracy obtained using the matrix of squares embodiment, the matrix of squares still has this advantage of the invention.

FIG. 8 shows another embodiment of the neural network in the present invention. The neural network has 3 outputs, i.e., OUT1, OUT2, and OUT3. Otherwise, this embodiment is the same as the embodiment explained above.

In order for the neural network to judge the particle patterns, each sample is presented to the neural network in the form of its 45 characteristics and 3 outputs, Out1, Out2, and Out3. If the agglutinated standard sample is used or the human judgement of a sample is agglutinated then the two desired outputs are Out1=1, Out2=0, and Out3=0. If the non-agglutinated standard sample is used or the human judgment of a sample is non-agglutinated, then the desired outputs are Out1=0, Out2=1, and Out3=0. If the uncertain standard sample is used or human judgment of a sample is uncertain, then the desired outputs are Out1=0, Out2=0, and Out3=1.

Once the neural network has been trained, it can be presented with new samples and it will make a determination of those samples based on a generalization made during its training. When the neural network is called upon to make a judgment it is presented with the 45 characteristics of a sample and a judgment can be determined from the values of its three outputs i accordance with Table 3.

TABLE 3

| OUT1 | OUT2 | OUT3 | JUDGMENT |
| --- | --- | --- | --- |
| 1 | 0 | 0 | + (positive) |
| 0 | 1 | 0 | − (negative) |
| 0 | 0 | 1 | ? |

Note:
+ means agglutination.
− means non-agglutination.
? means uncertain.

If the first output is the largest of the three outputs, then the particle pattern is judged to be agglutinated. If the second output is the largest of the three outputs, then the particle pattern is judged to be non-agglutinated. If the third output is the largest of the three outputs, then the particle pattern is judged to be uncertain. The neural network of this variation was trained with 67 sample particle patterns as same condition as the first embodiment explained above in Table 2. Then, 165 different samples with 79 uncertain judgments were tested with this variation. The result showed 96% judgment accuracy with a series of rings and 83% with a matrix of squares as in the first embodiment.

It will be appreciated by those skilled in the art that the present invention is not limited to the embodiment explained above, but that various alterations and modifications may be conceived by those skilled in the art without departing from the scope of the invention. In particular, the characteristics of the two-dimensional image of the particle patterns are not restricted to those used in the preferred embodiment. For instance, unequal spacing of the concentric rings may be utilized. If an inclined reaction vessel is used in place of a conically inclined reaction vessel then the concentric rings can be replaced with parallel lines as divisions of the characteristics describing the particle pattern.

What is claimed is:

1. A method for determining an agglutination reaction from a particle pattern formed on an inclined bottom surface of a reaction vessel comprising the steps of:
   scanning photoelectrically the inclined bottom surface to derive an image signal which represents a two-dimensional image of the particle pattern;
   processing the image signal into area light intensities by separating the inclined bottom surface into a plurality of areas due to different contours of the inclined bottom surface including decomposing the image signal into a series of concentric rings, each ring representing a different contour area of the image and integrating light intensities in each area to derive the area light intensities;
   determining an average intensity of each ring;
   inputting the area light intensities into a neural network to produce output signals; and
   determining an agglutination reaction based on the output signals.

2. The method according to claim 1, wherein the image signal is decomposed into 45 concentric rings.

3. A method of judging a particle pattern formed on a conically inclined bottom surface of a reaction vessel using a neural network, comprising the steps of:
   scanning photoelectrically the particle pattern to derive an image signal representing a two-dimensional image including the particle pattern;
   processing said image signal of the two-dimensional image to derive area light intensities representing different contours of the particle pattern including decomposing the image signal into a series of concentric rings, each ring representing a different contour area of the image;
   determining an average intensity of each ring;
   training a neural network with a standard sample; and
   judging the particle pattern with the trained neural network.

4. The method of judging according to claim 3, wherein the image signal is decomposed into 45 concentric rings.

* * * * *